United States Patent [19]

Meszaros et al.

[11] Patent Number: 5,107,045
[45] Date of Patent: Apr. 21, 1992

[54] PREPARATION OF 4-BROMO-O-XYLENE USING EXCESS BROMINE

[75] Inventors: Mark W. Meszaros, Batavia; Ibrahim Ghanayem, Downers Grove, both of Ill.

[73] Assignee: Amoco Corporation, Chicago, Ill.

[21] Appl. No.: 660,435

[22] Filed: Feb. 22, 1991

Related U.S. Application Data

[63] Continuation-in-part of Ser. No. 484,353, Feb. 22, 1990, Pat. No. 5,026,932.

[51] Int. Cl.$^5$ ............................................. C07C 17/12
[52] U.S. Cl. .................................... 570/206; 570/207; 570/209
[58] Field of Search ............... 570/206, 207, 208, 209, 570/210

[56] References Cited

U.S. PATENT DOCUMENTS

| | | | |
|---|---|---|---|
| Re. 32,606 | 2/1988 | Stepniczka | 570/206 |
| 2,452,154 | 10/1948 | Ross | 570/206 |
| 2,591,498 | 4/1952 | Betts et al. | 570/206 |
| 3,932,542 | 1/1976 | Gerns | 570/206 |
| 5,026,832 | 6/1991 | Meszaros | 570/206 |

Primary Examiner—Werren B. Lone
Attorney, Agent, or Firm—Thomas E. Nemo; William H. Magidson; Frank J. Sroka

[57] ABSTRACT

A regioselective process is provided for preparing 4-bromo-o-xylene in an isomer mixture of 4-bromo-o-xylene and 3-bromo-o-xylene by combining a molar excess of bromine with o-xylene. The produced 3-bromo-o-xylene isomer preferentially reacts with the excess bromine to produce dibromo-o-xylenes. The weight ratio of the 4-bromo-o-xylene to the 3-bromo-o-xylene in the product isomer mixture can be as high as about 97:3. Concurrent production of alpha-bromo-o-xylene is avoided by conducting the admixing in either darkness or in sulfur dioxide solution. The dibromo-o-xylene by products are easily separated by subsequent vacuum distillation or similar expedients.

20 Claims, No Drawings

PREPARATION OF 4-BROMO-O-XYLENE USING EXCESS BROMINE

This is a continuation-in-part application of application Ser. No. 484,353 filed on Feb. 22, 1990, U.S. Pat. No. 5,026,932.

FIELD OF THE INVENTION

This invention relates to regioselective bromination of of o-xylene to prepare 4-bromo-o-xylene using a molar excess of bromine.

BACKGROUND OF THE INVENTION

4-Bromo-o-xylene is useful in the preparation of diphenyl ethers. Illustrative such ethers are 3,3',4,4'-tetramethyldiphenyl ether, 1,4-bis(3,4-dimethylphenoxy)benzene, and the like. 4-Bromo-o-xylene is also useful as a starting reagent in some syntheses of riboflavin (vitamin $B_2$).

4-Bromo-o-xylene can be prepared from the reaction of 3,4-dimethylaniline with $CuBr_2NO$. This reaction proceeds through a diazonium intermediate, but such a preparation procedure is relatively costly, and is impractical on a large scale.

A route for commercial scale preparation of 4-bromo-o-xylene involves the addition of bromine ($Br_2$) to o-xylene. However, when one follows the solvent-less preparation procedure described in "Organic Syntheses", Vol. 3, pp 138, 139 (1955):

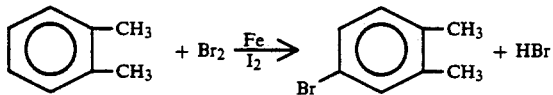

wherein the mole ratio of bromine to o-xylene is 0.875 and uses a temperature of 0° to −5° C., it is found by analysis that this procedure produces a 75:25 mixture of 4-bromo-o-xylene to 3-bromo-o-xylene in a 95 percent yield.

These two bromo-o-xylene isomers are extremely difficult to separate because they have virtually the same boiling point (214° C. for 4-bromo-o-xylene compared to 215° C. for 3-bromo-o-xylene). These isomers also cannot be separated by crystallization. They are also difficult to separate by gas chromatography (G.C.). A capillary G.C. column with cyanopropyl methyl silicone coating is needed to separate these isomers. It is therefore desirable to synthesize 4-bromo-o-xylene in as high a purity as possible to minimize the quantity of admixed 3-bromo-o-xylene present.

J. P. Canselier has reported (Bull.Soc.Chim. France, 1972, pp. 762–764, and Bull.Soc.Chim. France, 1971, pp. 1785–1788) achieving a 93.4:6.5 mixture of 4-bromo-o-xylene to 3-bromo-o-xylene by reacting a mixture of bromine, and o-xylene in $SO_2$ solution. The procedure for achieving a 93.4:6.5 mixture of 4-bromo-o-xylene to 3-bromo-o-xylene is not given but it is stated that it was run according to a process described for toluene, i.e., a mixture of bromine and sulfur dioxide is added to a very dilute mixture of the hydrocarbon at −40° C. and in a darkened reactor. The resulting mixture is then agitated at −9° C. for 3 hours before the sulfur dioxide is removed and the product isolated by distillation. His procedure is not suitable for commercial scale preparation of 4-bromo-o-xylene in high yields.

A process that produces 4-bromo-o-xylene in relatively high yield and in combination with a minimal amount of 3-bromo-o-xylene and other by-products would be commercially desirable. The present invention provides such a process.

SUMMARY OF THE INVENTION

A regiospecific process for producing an isomer mixture rich in 4-bromo-o-xylene is provided wherein bromine is combined with o-xylene within a bromine-to-o-xylene mole ratio range of more than about 1:1 and up to about 2:1 while maintaining the resulting admixture at a temperature in the range of about −20° C. to about 40° C.

The use of a molar excess of bromine relative to o-xylene enhances the weight ratio of 4-bromo-o-xylene to 3-bromo-o-xylene in the mixed isomer reaction product. The excess bromine preferentially reacts with the 3-bromo-o-xylene isomer to produce dibromo-o-xylene isomers which results in an enrichment of 4-bromo-o-xylene in the produced bromo-o-xylene isomer mixture.

To enhance yields and minimize by-product formation, the reaction of the process is preferably conducted either shielded from actinic radiation or in a liquid sulfur dioxide solvent.

It is presently preferred to employ a bromine ($Br_2$) to o-xylene mole ratio of about 1.5:1 and to employ a reaction temperature in the range of about −9° C. to about −15° C. Preferably, the bromine is slowly added to the o-xylene with agitation, and, preferably, after such addition is completed, the agitation is continued for a period of time while a product mixture is produced.

The product isomer mixture is separable from the reaction product by vacuum distillation.

Various other and further features, embodiments, and the like which are associated with the present invention will become apparent and better understood to those skilled in the art from the present description.

DETAILED DESCRIPTION OF PREFERRED EMBODIMENTS

The bromination reaction of the present invention is carried out under liquid phase conditions. Bromine ($Br_2$) is combined with o-xylene within a bromine to o-xylene respective mole ratio range of more than about 1:1 and up to about 2:1 while maintaining the resulting admixture at a temperature in the range of about −20° C. to about 40° C.

A presently preferred such mole ratio range of bromine to o-xylene is about 1.1:1 to about 1.5:1. A particularly preferred such mole ratio is about 1.5:1, respectively. A presently preferred reaction temperature ranges from about −9° C. to about −15° C.

The reaction can be carried out, if desired, in the presence of a Lewis acid catalyst, such as an iron halide. If employed, a catalytically effective amount of such catalyst is used. For example, a suitable amount of such catalyst is in the range of about 0.01 to about 0.1 equivalents of catalyst per equivalent of o-xylene.

The reaction appears to be sensitive to actinic radiation. Exposure of the reactants to such radiation appears to promote production of a by-product, alpha-bromo-o-xylene.

Alpha-bromo-o-xylene is an undesirable by-product since not only does it reduce yields of the desired 4-bromo-o-xylene based on starting o-xylene, but also it is difficult to separate by distillation inasmuch as alphabromo-o-xylene has a similar boiling point (217° C.) to that of 4-bromo-o-xylene and 3-bromo-o-xylene.

To minimize production of such by-product, the reaction in accord with this invention can be shielded from actinic radiation. Alternatively, and for the same purpose, this reaction can be conducted in a liquid sulfur dioxide medium.

If conducted in sulfur dioxide medium, the mole ratio of sulfur dioxide to o-xylene is at least about 0.1:1, preferably at least about 1:1, and is most preferably at least about 2:1 and also most preferably not more than about 30:1. Each of the o-xylene and the bromine can be preliminarily dissolved in the sulfur dioxide, if desired, or one or the other of such reactants can be preliminarily so dissolved and the other of such reactants can be added directly thereto with mixing. A present preference is to add bromine to a solution of o-xylene in sulfur dioxide.

For example, when o-xylene is brominated under solvent-less conditions at −10° C. without blackening the reaction flask or trying to keep all actinic radiation (e.g., light) out, up to about 10 percent alpha-bromo-o-xylene is produced. Under identical conditions, except for the use of $SO_2$ as a solvent, only about 0.3 percent alpha-bromo-o-xylene is produced.

In addition to reducing the amount of alpha-bromo-o-xylene formed, the use of sulfur dioxide as a solvent for o-xylene, bromine, and bromo-o-xylene isomers is desirable because it produces relatively greater regioselectivity favoring 4-bromo-o-xylene production compared to other known solvents or catalysts. Sulfur dioxide also decreases the bromination of aromatic side chains and aids in achieving high yields of 4-bromo-o-xylene.

Sulfur dioxide refluxes (boils) at about −9° C. at atmospheric pressure. Such a temperature constitutes a particularly convenient reaction temperature for practicing the process of this invention when sulfur dioxide is used as a solvent. When the reaction is carried out at more elevated temperatures, the reaction zone can be maintained under autogenous pressure to maintain $SO_2$ in liquid state. Pressures up to about 4 atmospheres are convenient. At 0° C. the $SO_2$ vapor pressure is about 20 psig, and at ambient temperature, about 40 psig.

At the end of a given reaction of bromine with o-xylene, and before a subsequent purification of a resulting liquid reaction product mixture, the sulfur dioxide, if used, can be easily separated by warming a product solution to vaporize the sulfur dioxide and venting same. Concurrently, any by-product HBr produced in this reaction can be removed as well.

While any admixing technique can be employed for the bromine and o-xylene, it is presently preferred to add, slowly and with mixing, the bromine to the o-xylene, whether or not sulfur dioxide dissolution is involved. Preferably, however, the o-xylene is first dissolved in the sulfur dioxide and the bromine is added thereto with stirring. A presently preferred bromine addition rate is about 0.5 to about 2.5 moles of bromine per hour per mole of o-xylene, and more preferably, about 1.4 to about 1.8 moles of bromine per hour per mole of o-xylene.

After the admixture of bromine with o-xylene is complete, it is presently preferred to continue to agitate the reaction mixture at a temperature within the range indicated to optimize the conversion of the starting reactants. The post-addition agitation time period usually is about 0.05 to about 4.5 hours, preferably being at least about ½ hour when no sulfur dioxide solvent is used, and not more than about 1 hour when sulfur dioxide is used as solvent.

It is presently preferred that each of the reactants, and also each of the other components present in a reaction, such as liquid sulfur dioxide (if employed), or catalyst (if employed), have a purity of at least about 95 weight percent, and more preferably a purity of at least about 99 weight percent, since such purity levels enhance yields of 4-bromo-o-xylene. For example, if a small amount of m-xylene is present with the o-xylene, as is common in many commercially available o-xylenes, the m-xylene reacts with the bromine to produce a small amount of 4-bromo-m-xylene which, in turn, reduces the yield of 4-bromo-o-xylene.

As indicated above, a particular feature of the present invention is the provision of a regiospecific process favoring production of 4-bromo-o-xylene. The product of the process of this invention is a bromo-o-xylene isomer mixture comprised of 4-bromo-o-xylene and 3-bromo-o-xylene wherein the weight ratio of the former relative to the latter has been enhanced through the use of a stoichiometric excess of bromine relative to o-xylene.

As shown in Table I below, various weight ratios of 4-bromo-o-xylene to 3-bromo-o-xylene were obtained for particular mole ratios of bromine to o-xylene at various reaction temperatures.

For illustration, in Examples 1–9 below, the preferred procedure of slow addition of bromine to o-xylene was employed within the addition rate range above indicated with continuous mixing. After bromine addition was completed, mixing was continued for a time of about 0.2 hours. Solvent-less conditions were employed with the reaction zone being maintained in darkness.

TABLE I

| Weight Ratios of 4-Bromo-o-Xylene to 3-Bromo-o-Xylene Achieved at Various Reaction Temperatures | | | | |
|---|---|---|---|---|
| Run | Ex. No. | T, °C. | $Br_2$:o-Xylene Mole Ratio | 4-BOX:3-BOX Weight Ratio |
| A | 1 | 40 | 0.9:1 | 75:25 |
| B | 4 | 0 | 0.6:1 | 75:25 |
| C | 7 | −15 | 0.7:1 | 80:20 |
| D |   | −15 | 0.9:1 | 80:20[2] |
| E | 3 | RT[1] | 1.5:1 | 87:13 |
| F | 6 | 0 | 1.5:1 | 90:10 |
| G | 9 | −15 | 1.5:1 | 94:6 |
| H | 2 | RT[1] | 1.3:1 | 81:19 |
| I | 8 | −15 | 1.3:1 | 87:13 |

Table I Footnotes:
[1]RT designates room temperature.
[2]No catalyst

As the data in Table I and Examples 1–9 below demonstrate, when a molar excess of bromine relative to o-xylene is used at any given reaction temperature within the range herein indicated, even greater weight ratios of 4-bromo-o-xylene to 3-bromo-o-xylene are achieved than when equimolar ratios of bromine to o-xylene are employed. The excess bromine reacts with the brom-o-xylene isomer mixture to produce dibromo-o-xylene isomers. Among such latter isomers, the major isomer found to be produced has been identified as 4,5-dibromo-o-xylene. Due to inherent steric and electronic effects, 3-bromo-o-xylene is more reactive towards bromine than 4-bromo-o-xylene and the 3-bromo-o-xylene is preferentially consumed and converted to dibromo-o-xylenes. The result is an enrichment of 4-dibromo-o-xylene in the final bromo-o-xylene isomer mixture. The following equations are illustrative:

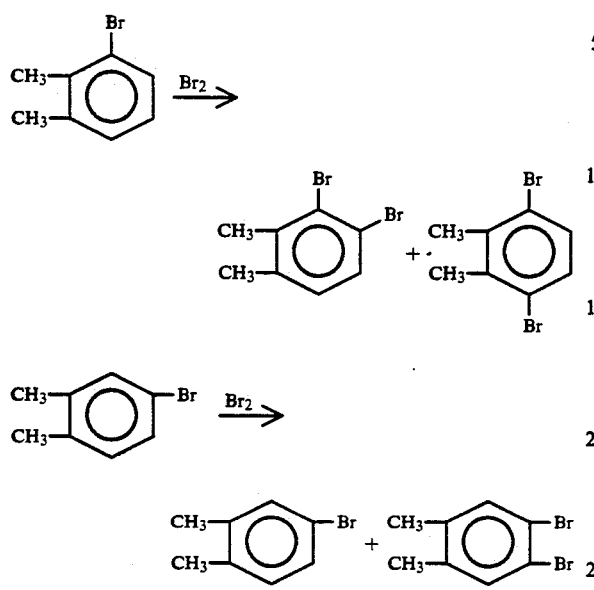

For example, as shown in Table I, a solventless (i.e., without sulfur dioxide) reaction using equimolar proportions of reactants and involving the preferred procedure of slow bromine addition with stirring (mixing) to o-xylene at −15° C. produces an 80:20 weight ratio mixture of 4-bromo-o-xylene to 3-bromo-o-xylene. However, a Br$_2$:o-xylene mole ratio of 1.5:1 under the same conditions produces a surprising 94:6 weight ratio mixture of 4-bromo-o-xylene to 3-bromo-o-xylene. Such a reaction of excess bromine with o-xylene also gives improved regioselectivities favoring 4-bromo-o-xylene relative to 3-bromo-o-xylene at other temperatures, such as 0° C., as shown in Table I. A maximized production of 4-bromo-o-xylene with such a bromine excess is observed at −15° C. using a 50 percent molar excess of bromine beyond stoichiometry.

Similar outstanding enrichment of 4-bromo-o-xylene relative to 3-bromo-o-xylene in a product isomer mixture having a weight ratio as high as about 97:3 is also achieved with such a molar excess of bromine relative to o-xylene when a sulfur dioxide solvent is used. Preferably, the o-xylene is preliminarily dissolved in the sulfur dioxide and the bromine is slowly directly added to such solution.

Concurrently, yields of 4-bromo-o-xylene based on starting o-xylene are desirably high, being commonly in the range of about 25% to about 85% in the direct solventless reaction achieved by the indicated slow addition of bromine to o-xylene, and commonly in the range of about 50% to about 85% in the indicated procedure of slow addition of bromine to such a sulfur dioxide solution of o-xylene.

Product isomer mixtures of 4-bromo-o-xylene and 3-bromo-o-xylene are isolatable from a liquid reaction product by vacuum distillation.

By using such a molar excess of bromine as taught herein for the reaction with o-xylene, higher ratios of 4-bromo-o-xylene to 3-bromo-o-xylene in such a purified product isomer mixture are obtained at reaction temperatures within the range taught herein than any previously reported 4-bromo-o-xylene preparation, particularly from the reaction of bromine with o-xylene. Depending upon the exact mole ratio of Br$_2$ to o-xylene, the reaction temperature, the mixing procedure, and other variables, the bromo-o-xylene isomer mixtures produced by the practice of the process of this invention have weight ratios of 4-bromo-o-xylene to 3-bromo-o-xylene which fall in the range of more than about 80:20 to about 97:3.

The following examples are offered to specifically illustrate the invention. These examples are not to be construed as limiting the scope thereof, however. In these examples, "4-BOX" designates 4-bromo-o-xylene, "3-BOX" designates 3-bromo-o-xylene, "4-BMX" designates 4-bromo-m-xylene, "A-BOX" designates alpha bromo-o-xylene, "DiBOX" designates dibromo-o-xylene, "4:3-BOX" designates ratio of 4-bromo-o-xylene to 3-bromo-o-xylene, "o-X" designates o-xylene, "Br$_2$" designates bromine, "Cat" designates catalyst, "T" designates temperature in degrees centigrade, and "o-X Conc." designates molar concentration of o-xylene reactant in SO$_2$.

EXAMPLES 1–9

Reaction of Bromine with o-Xylene

A series of o-xylene brominations was performed in the following manner. A three-neck flask equipped with a dry ice condenser, addition funnel, and septum was cooled to −15° C. with a cold bath. The flask was wrapped in foil to prevent the light catalyzed formation of alpha-bromo-o-xylene. The bromine was added slowly (usually over about a 60 min. time period) via the addition funnel to o-xylene in the flask. The addition rate was thus approximately about 1 mole of bromine per hour per mole of o-xylene. After addition was completed, the reaction solution stirred for an additional 90 min. at −15° C. before the solution was warmed to ambient temperature. The results are shown in Table II below. A small amount of 4-bromo-m-xylene (4-BMX) was found to be always produced due to small amounts of m-xylene present in the starting o-xylene (which was about 97 percent pure).

In Example 9, bromine (120 g, 0.75 mol) was added to o-xylene (53 g, 0.5 mol) at −15° C. Iron filings (0.5 g) and iodine (0.5 g) were used to provide the catalyst. The addition of bromine took 1 hour and the reaction mixture was thereafter stirred for an additional 4.5 hours before the reaction was complete. The reaction mixture was warmed to room temperature, filtered, and washed with 1N aqueous NaOH. The resulting liquid, analyzed by gas chromatography, contained 3.3 percent 3-BOX, 50.4 percent 4-BOX, and 45.8 percent DiBOX isomers. Fractional distillation gave a principal fraction containing 6.0 percent 3-BOX, 88.9 percent 4-BOX, and 4.5 percent DiBOX isomers for an isolated yield of 25 percent starting from o-xylene for such an isomer mixture.

In Example 3, bromine (240 g, 1.5 mol) was added to o-xylene (106 g, 1 mol) at ambient temperature. Iron filings (0.7 g) and iodine (0.4 g) were used as catalysts. The addition of bromine took 1.5 hour and the reaction mixture was thereafter stirred for an additional 1 hour. The reaction mixture contained 6.9 percent 3-BOX, 44.7 percent 4-BOX, and 47.9 percent DiBOX isomers at this time. After distillation, an 87:13 mixture of 4:3-BOX was obtained in 40 percent isolated yield for such isomer mixture from o-xylene.

TABLE II

Summary of Data for Examples 1–9

| Ex. No. | GC Analysis (Area %) | | | | | Weight Ratio 4:3-BOX | grams | | mmol | | Cat. | T, °C. | Mole Ratio Br$_2$/o-X |
|---|---|---|---|---|---|---|---|---|---|---|---|---|---|
| | 4-BMX | 3-BOX | 4-BOX | A-BOX | DiBOX | | o-X | Br$_2$ | o-X | Br$_2$ | | | |
| 1 | 1.3 | 23.4 | 71.8 | — | 3.5 | 75:25 | 13.2 | 17.8 | 124 | 111 | Fe/I$_2$** | 40 | 0.9 |
| 2 | 0.7 | 13.0 | 57.1 | — | 29.2 | 81:19 | 106.2 | 208.0 | 1000 | 1300 | Fe/I$_2$ | RT* | 1.3 |
| 3 | 0.5 | 6.9 | 44.7 | — | 47.9 | 87:13 | 106.0 | 240.0 | 1000 | 1500 | Fe/I$_2$ | RT* | 1.5 |
| 4 | 2.0 | 21.1 | 75.9 | 0.2 | 1.0 | 75:25 | 28.0 | 26 | 264 | 163 | I$_2$ | | 0.6 |
| 5 | 1.3 | 24.5 | 68.2 | — | 5.4 | 74:26 | 50.0 | 60.6 | 470 | 380 | Fe/I$_2$ | | 0.8 |
| 6 | 0.4 | 5.7 | 49.1 | — | 44.8 | 90:10 | 20.0 | 45.0 | 189 | 281 | Fe/I$_2$ | | 1.5 |
| 7 | 1.5 | 18.9 | 74.8 | 0.1 | 4.7 | 80:20 | 10.0 | 11.2 | 94 | 70 | Fe/I$_2$ | −15 | 0.7 |
| 8 | 0.8 | 10.0 | 68.1 | — | 21.1 | 87:13 | 53.0 | 104.0 | 500 | 650 | Fe/I$_2$ | −15 | 1.3 |
| 9 | 0.5 | 3.3 | 50.4 | — | 45.8 | 94:6 | 53.0 | 120.0 | 500 | 750 | Fe/I$_2$ | −15 | 1.5 |

Table II Footnotes:
*"RT" designates room temperature
**In these examples, the weight ratio of Fe to I$_2$ was 1:1, and the Fe was in the form of filings.

As the data in Table II (above) shows, for Br$_2$/o-X mole ratios greater than about 1:1, the weight ratio of 4-BOX to 3-BOX is unexpectedly increased with a concurrent significant increase in the production of by-product DiBOX.

Since the boiling temperature of DiBOX significantly differs from that of 4-BOX and 3-BOX, DiBOX is easily separated from the isomer mixture of 4-BOX and 3-BOX by using vacuum distillation conditions such as hereinabove characterized.

EXAMPLES 10–21

Reaction of Bromine with o-Xylene in Sulfur Dioxide

A series of o-xylene brominations in sulfur dioxide was performed in the following manner. A 100 ml three neck flask equipped with a dry ice condenser and cooled to −78° C. with a dry ice/acetone cold bath. The liquid SO$_2$ was added through a stopcock adapter. After the addition was complete, the SO$_2$ was warmed to −15° C., and o-xylene was added through the addition funnel and dissolved with mixing in the sulfur dioxide. The bromine was then added slowly with continuous stirring at a rate estimated to be about 2 moles bromine per hour per mole of o-xylene (usually over a 30 minute period) through the addition funnel. The reaction solution was kept at −15° C. using a cold bath. The reaction solution was continuously stirred after such addition for an additional 10 min. at −15° C. before the solution was warmed and the SO$_2$ removed by evaporation. Table 3 below shows the results.

Examples 17, 18 and 19 were each run with a molar excess of bromine relative to o-xylene. With the excess bromine, bromination of the bromo-o-xylenes occur and the 3-BOX is preferentially brominated over the 4-BOX isomer. This produces greater enrichment of the 4-BOX isomer present in the product mixture. The bromo-o-xylene mixture is subsequently easily separated from the dibromo-o-xylenes by vacuum distillation (exemplary conditions).

In Example 20, a Fischer-Porter bottle was filled with SO$_2$ (62 g, 41 ml) and o-xylene (8 g, 75 mmol) and cooled to 0° C. with an ice water bath. The pressure was 20 psig due to the SO$_2$ partial pressure at that temperature. After the bromine (9 g, 56 mmol) was completely added, the reaction mixture was stirred for an additional 10 minutes. The resulting mixture of bromo-o-xylene was 90:10 4:3-BOX.

It is estimated on the basis of the results in Examples 20 and 21 that if these Examples were run with excess Br$_2$ then the 4:3-BOX weight ratio would increase.

In Example 21, a Fischer Porter bottle was filled with SO$_2$ (53 g, 35 ml) and o-xylene (10 g, 94 mmol) and placed in a water bath at 20° C. The pressure was 43 psig due to the SO$_2$ partial pressure at that temperature. After the bromine (7 g, 44 mmol) was completely added, the reaction mixture was stirred for an additional 10 minutes. The resulting mixture of bromo-o-xylenes was 90:10 4-BOX:3-BOX.

The 4-BOX:3-BOX product was isolated in Example 16. After the SO$_2$ and HBr were removed by evaporation, the reaction product was washed with 0.1N aqueous NaOH solution (250 ml), and twice with H$_2$O (125 ml each). The organic layer was dried over MgSO$_4$. No further purification was necessary. The isolated yield was 75 g (405 mmol, 80 percent yield).

For a product of Example 19 made with a molar excess of Br$_2$, it is estimated that a product yield of about 75% would be obtained.

TABLE III

Summary of Data for Examples 10–21

| Ex. No. | GC Analysis (Area %) | | | | | Weight Ratio 4:3-BOX | Mole Ratio BR$_2$/o-X | grams | | | mmol | | | ml liq. SO$_2$ | mol SO$_2$ mol o-X | o-X Conc., M | T, °C. |
|---|---|---|---|---|---|---|---|---|---|---|---|---|---|---|---|---|---|
| | 4-BMX | 3-BOX | 4-BOX | A-BOX | DiBOX | | | o-X | Br$_2$ | SO$_2$ | o-X | Br$_2$ | SO$_2$ | | | | |
| 10 | 1.1 | 7.3 | 86.4 | — | 2.65 | 92:8 | 1 | 10.0 | 15.1 | 60 | 94 | 94 | 40 | 9.95 | 1.82 | −15 |
| 11 | 1.8 | 10.2 | 79.8 | 0.1 | 1.7 | 88:12 | 1 | 10.0 | 15.1 | 16 | 94 | 94 | 11 | 2.66 | 4.16 | −15 |
| 12 | 1.1 | 9.2 | 82.3 | — | 1.9 | 90:10 | 1.01 | 10.0 | 15.2 | 32 | 94 | 95 | 21 | 5.32 | 2.88 | −15 |
| 13 | 1.0 | 12.0 | 63.7 | — | 0.4 | 84:16 | 0.88 | 27.0 | 36.0 | 19 | 255 | 255 | 13 | 1.16 | 5.74 | −15 |
| 14 | 1.6 | 9.0 | 87.6 | 0.3 | 1.3 | 90:10 | .85 | 8.5 | 11.0 | 27 | 80 | 68 | 18 | 5.25 | 2.86 | −15 |
| 15 | 1.5 | 8.1 | 89.6 | 0.15 | 0.8 | 92:8 | .78 | 70.0 | 82.1 | 385 | 660 | 514 | 257 | 9.09 | 1.95 | −15 |
| 16 | 1.3 | 8.0 | 77.9 | — | 0.8 | 91:9 | .805 | 67.0 | 81.3 | 381 | 632 | 509 | 254 | 9.41 | 1.9 | −15 |
| 17 | 1.1 | 7.5 | 86.6 | 0.1 | 4.0 | 92:8 | 1.12 | 4.6 | 7.7 | 65 | 43 | 48 | 43 | 23.5 | 0.9 | −15 |
| 18 | 0.9 | 4.9 | 79.0 | — | 15.1 | 94:6 | 1.23 | 5.0 | 9.8 | 70 | 47 | 61 | 47 | 23.2 | 0.9 | −15 |
| 19 | 1.0 | 6.2 | 83.8 | — | 8.5 | 93:7 | 1.23 | 27.0 | 53.8 | 255 | 255 | 331 | 170 | 15.6 | 1.27 | −15 |
| 20 | 2.0 | 9.6 | 86.9 | — | 1.0 | 90:10 | .75 | 8.0 | 9.0 | 62 | 75 | 56 | 41 | 12.9 | 1.5 | 0 |

TABLE III-continued

Summary of Data for Examples 10-21

| Ex. No. | GC Analysis (Area %) | | | | | Weight Ratio 4:3-BOX | Mole Ratio BR$_2$/o-X | grams | | | mmol | | | ml liq. SO$_2$ | mol SO$_2$ mol o-X | o-X Conc., M | T, °C. |
|---|---|---|---|---|---|---|---|---|---|---|---|---|---|---|---|---|---|
| | 4-BMX | 3-BOX | 4-BOX | A-BOX | DiBOX | BOX | | o-X | Br$_2$ | SO$_2$ | o-X | Br$_2$ | SO$_2$ | | | | |
| 21 | 3.2 | 10.2 | 84.5 | — | 1.0 | 89:11 | .47 | 10.0 | 7.0 | 53 | 94 | 44 | 35 | 8.83 | | 2.0 | 20 |

EXAMPLES 22-26

Effect of Concentration on Selectivity

Using a procedure similar to that employed in Examples 10-21, 92:8 4:3-BOX mixtures were prepared using equimolar bromine and o-xylene in SO$_2$, as shown in the following Table IV. The concentration of reactants in SO$_2$ was found to slightly affect the selectivity. A 1.95 molar solution (70 g of oxylene in 260 ml of SO$_2$) gave a ratio of 92:8 4-BOX:3-BOX whereas a 2.86 molar solution gave a ratio of 90:10/4:3-BOX. Increasing the concentration decreased the selectivity; thus, a 4.16 molar solution gave a ratio of 88:12/4:3-BOX, and a 5.74 molar (27 g o-xylene in 13 ml SO$_2$) gave a ratio of 84:16 4:3-BOX. The excellent selectivity at this concentration is surprising. The SO$_2$ is no longer acting as a solvent, but as a catalyst.

TABLE IV

Summary of Data for Examples 22-26

| Ex. No. | mmol. o-X | mmol. Br$_2$ | SO$_2$ (ml) | o-X Conc., M | T, °C. | Ratio 4:3-BOX |
|---|---|---|---|---|---|---|
| 22 | 43 | 48 | 43 | 0.9 | −15 | 92:8 |
| 23 | 660 | 514 | 260 | 1.95 | −15 | 92:8 |
| 24 | 80 | 68 | 18 | 2.86 | −15 | 90:10 |
| 25 | 94 | 94 | 11 | 4.16 | −15 | 88:12 |
| 26 | 255 | 225 | 13 | 5.74 | −15 | 84:16 |

EXAMPLES 27-29

Effect of Overbromination on Selectivity

When a 50% excess of bromine was used a 4:3-BOX mixture as high as 97:3 was obtained. Such increased selectivity to 4-BOX is the result of a slight preference in the bromination of 3-BOX over 4-BOX. Such overbromination in SO$_2$ is substantially cleaner than the overbromination in neat o-xylene. The major product in the SO$_2$ overbromination is 4,5-dibromo-o-xylene which crystallizes upon standing.

The procedure was similar to that employed in Examples 10-21 and the results are shown in the following Table V.

TABLE V

Summary of Data for Examples 27-29

| Ex. No. | mmol. o-X | mmol. Br$_2$ | SO$_2$ (ml) | Ratio Br$_2$:o-X | T, °C. | Ratio 4:3-BOX |
|---|---|---|---|---|---|---|
| 27 | 125 | 188 | 125 | 1.5:1 | −15 | 96:4 |
| 28 | 400 | 600 | 400 | 1.5:1 | −10 | 97:3 |
| 29 | 125 | 190 | 125 | 1.5:1 | −10 | 96:4 |

Separation of 4-bromo-o-xylene from 3-bromo-o-xylene in an isomer mixture was accomplished using a Hewlett Packard 5890 gas chromatograph equipped with a 50m by 0.25 mm inside diameter CPS-1 capillary column which contains a cyanopropyl methyl silicone film.

The most effective temperature program was an initial temperature of 100° C. followed by a 4° C. per minute temperature increase up to 180° C. final temperature.

Reaction products were identified by (a) gas chromatography-mass spectroscopy; and (b) comparison of retention times with that of authentic samples. Also, $^1$H and $^{13}$C NMR (nuclear magnetic resonance) were used to verify the structure of 4-BOX.

The foregoing specification is intended as illustrative and is not to be taken as limiting. Still other variations within the spirit and the scope of the invention are possible and will readily present themselves to those skilled in the art.

That which is claimed is:

1. A regioselective process for producing an isomer mixture comprising 3-bromo- and 4-bromo-o-xylene wherein said isomer mixture is rich in 4-bromo-o-xylene which process comprises combining bromine with o-xylene in a reaction zone within a bromine to o-xylene mole ratio range of more than about 1:1 to about 2:1, respectively, while maintaining the resulting admixture at a temperature in the range of about −20° C. to about 40° C. to produce a product mixture.

2. The process of claim 1 wherein said reaction zone is shielded from actinic radiation.

3. The process of claim 1 wherein said combining is conducted in a liquid sulfur dioxide medium.

4. The process of claim 3 wherein said sulfur dioxide is present in an amount such that the mole ratio of sulfur dioxide to o-xylene is at least about 1:1.

5. The process of claim 3 wherein said sulfur dioxide is present in an amount such that the mole ratio of sulfur dioxide to o-xylene is in the range of about 2:1 to about 30:1.

6. The process of claim 3 wherein said sulfur dioxide is present in an amount such that the mole ratio of sulfur dioxide to o-xylene is in the range of about 5.2:1 to about 23.5:1.

7. The process of claim 1 wherein said combining is carried out in the presence of a Lewis acid catalyst.

8. The process of claim 1 wherein said mole ratio of said bromine to said o-xylene is about 1.1:1 to about 1.5:1.

9. The process of claim 1 wherein said mole ratio is about 1.5:1.

10. The process of claim 1 wherein said combining is accomplished by gradually adding said bromine with stirring to said o-xylene at an addition rate in the range of about 0.5 to about 1.5 moles of bromine per hour per mole of o-xylene to produce said admixture.

11. The process of claim 10 wherein, after said combining is completed, the resulting admixture is agitated for a time period in the range of about 0.05 to about 4.5 hours.

12. The process of claim 10 wherein said o-xylene is first dissolved in sulfur dioxide prior to said combining, and wherein said sulfur dioxide is present in a mole ratio of said sulfur dioxide to said o-xylene of at least about 1:1, and wherein said admixture is agitated for a period of time of about 0.05 to about 0.5 hour to produce a product mixture.

13. The process of claim 1 further comprising subjecting said product mixture to vacuum distillation to isolate said isomer mixture.

14. The process of claim 1 wherein said temperature is in the range of about −9° C. to about −15° C. and said bromine is added to said o-xylene.

15. The process of claim 3 wherein said sulfur dioxide is maintained at its reflux temperature during said combining.

16. The process of claim 3 wherein the resulting admixture is maintained at a temperature of about −15° C.

17. The process of claim 3 wherein said admixture is maintained under autogenous pressure at a temperature above about −9° C.

18. The process of claim 12 wherein said product mixture is warmed to an extent sufficient to evaporate said sulfur dioxide and produce a liquid reaction product.

19. The process of claim 18 wherein said liquid reaction product is subjected to vacuum distillation to isolate said isomer mixture.

20. The process of claim 1 wherein said isomer mixture is passed through a capillary gas chromatography column which has been precoated with cyanopropyl methyl silicone to separate 4-bromo-o-xylene from at least 3-bromo-o-xylene.

* * * * *

UNITED STATES PATENT AND TRADEMARK OFFICE
CERTIFICATE OF CORRECTION

PATENT NO. : 5,107,045
DATED : 4/21/92
INVENTOR(S) : Meszaros, et al

It is certified that error appears in the above-indentified patent and that said Letters Patent is hereby corrected as shown below:

| Column | Line |
|---|---|
| 1 | line 11, "of of o-xylene to prepare" should read -- of o-xylene to prepare -- |
| 8 | Cols. 13 and 14 of Chart, ".6" should read -- 0  .6 -- |
| 8 | Cols. 13 and 14 of Chart, ".8" should read -- 0  .8 -- |
| 8 | Cols. 13 and 14 of Chart, "1.5" should read -- 0  1.5 -- |
| 9 | line 18, "70 g of oxylene" should read -- 70 g of o-xylene -- |

Signed and Sealed this

Seventh Day of September, 1993

Attest:

BRUCE LEHMAN

*Attesting Officer*  *Commissioner of Patents and Trademarks*